United States Patent [19]

Wilson et al.

[11] Patent Number: 5,043,141

[45] Date of Patent: Aug. 27, 1991

[54] INJECTION SYSTEMS FOR SAMPLE TESTING FOR LUMINOMETERS

[75] Inventors: Stuart Wilson, Enfield, England; Clive Goodfield, Mid Glamorgan, Wales; David A. Stafford, Cardiff, Wales; Ian R. Johnson, Mid Glamorgan, Wales

[73] Assignee: Cardiff Laboratories for Energy & Resources Limited, Cardiff, Wales

[21] Appl. No.: 267,163

[22] Filed: Oct. 24, 1988

[30] Foreign Application Priority Data

Oct. 29, 1987 [GB] United Kingdom ............... 8725380

[51] Int. Cl.$^5$ .......................................... G01N 21/76
[52] U.S. Cl. ...................... 422/52; 422/100; 73/864.21; 73/864.25; 73/864.86; 73/864.87
[58] Field of Search ............. 436/54, 180; 422/99, 422/100, 68, 52; 356/36, 218; 73/864.21, 864.24, 864.25, 864.85, 864.86, 864.87

[56] References Cited

U.S. PATENT DOCUMENTS

| 3,559,703 | 2/1971 | Maul et al. ...................... 73/864.86 |
| 3,566,698 | 3/1971 | Sheppard ......................... 73/864.85 |
| 3,581,573 | 6/1971 | Purcell et al. ................... 73/864.86 |
| 3,672,226 | 6/1972 | Reid ............................... 73/864.86 |
| 3,693,455 | 9/1972 | Harding et al. .................. 73/864.86 |
| 3,849,653 | 11/1974 | Sakaide et al. .................. 422/52 |
| 3,884,802 | 5/1975 | Spaans et al. ................... 73/864.85 |
| 4,495,149 | 1/1985 | Iwata et al. ...................... 422/99 |
| 4,539,855 | 9/1985 | Jacobs ............................. 73/864.25 |
| 4,755,055 | 7/1988 | Johnson et al. .................. 356/440 |
| 4,757,437 | 7/1988 | Nishimura ....................... 73/864.25 |
| 4,808,381 | 2/1989 | McGregor et al. ............... 422/100 |
| 4,854,181 | 8/1989 | Gerstel ............................ 73/864.87 |

Primary Examiner—Richard V. Fisher
Assistant Examiner—Todd J. Burns
Attorney, Agent, or Firm—Young & Thompson

[57] ABSTRACT

An injection system for use with a luminometer, which includes a carrier movable between a liquid loading station and a liquid dispensing station and a dispenser assembly mounted on the carrier and including an injector needle arranged, when at the liquid loading station, to pass through an aperture in a part of the luminometer aligned with a test sample container therein, the container being in a test chamber with which a photomultiplier device communicates. The system also includes a sealing arrangement which prevents light from passing through the aperture in the luminometer, both when the needle extends through the aperture and when the needle has been withdrawn from the aperture.

6 Claims, 3 Drawing Sheets

INJECTION SYSTEMS FOR SAMPLE TESTING FOR LUMINOMETERS

INTRODUCTION

This invention relates to injection systems for use in luminometers for sample testing. A luminometer is a device for measuring light photons, particularly at low light levels, produced by bio-luminescent or chemi-luminescent effects. The luminometer construction with which the invention is concerned is designed to detect and measure light emission produced as a result of chemical or other reactions, the measurement being translated into a signal which may take one of many forms, according to particular tests being undertaken.

Typical circumstances in which the luminometer may be used include testing of samples of liquids to determine various factors, the device being useful in medical applications, or in the food and drink, pharmaceutical, water treatment, or other industries. It may also be used for research in various fields.

The luminometer has means for presenting a sample, in the form of a liquid or a liquid suspension, and normally in a transparent tube or cuvette, to a photo-multiplier device by means of which the actual measurement is carried out.

It may be necessary to prepare the sample, before presentation to the photo-multiplier device, in various ways, depending upon the nature of the sample and upon the requirements of the test to be conducted. This preparation may include extraction of ATP (adenosine-5'-triphosphate) molecules, adding suitable reagents, reactants, or the carrying out of other processes to produce light emissions of sufficient intensity to be detectable and measurable by the photo-multiplier device. Certain functions, moreover, may be carried out while the sample is presented to the photo-multiplier device.

Such a luminometer, to which the invention is applicable is described and claimed in published European Patent Application No. EP 0226374.

Injection or dispensing systems whereby reagents, reactants, or other liquids may be added to the sample, while this sample is in the luminometer, have been proposed. A system tried in the luminometer described in the above mentioned European patent application included means whereby liquids could be injected directly into the cuvettes containing the samples, this being carried out while a sample, in a cuvette, was situated in a chamber with which the photo-multiplier communicated, thus enabling reactions, producing light emissions, to take place in front of the photo-multiplier device. This system included multiple individual injectors for respective materials, and was therefore limited to a small number of injectors, normally about three, in view of the very limited space availability.

The system referred to in the patent specification was not therefore particulary versatile or efficient, and gave rise to certain problems, particularly concerning the requirement to exclude light from the chamber in which the sample was situated, when exposed to the photo-multiplier device.

There are certain problems to be overcome in introducing and removing cuvettes from the chamber with which the photo-multiplier device communicates. In particular, stray extraneous light or other discharges must be excluded from the chamber during the test period, since these could adversely affect the accuracy of detection of the light photons by the highly sensitive photo-multiplier device, and yet the cuvettes must be easily and quickly introduced into the chamber and removed from it, preferably without the need for elaborate screening means. Light collection should also be maximised within the chamber in order to provide the best possible conditions for accurate measurement.

SUMMARY OF THE INVENTION

It is the object of the invention to provide an injector system for a luminometer which is versatile and efficient, and in which the risk of extraneous light entering the chamber in which the sample is exposed to the photo-multiplier tube is minimised.

In accordance with the present invention there is provided an injector system for use with a luminometer, comprising a movable carrier, there being at least two stations between which the carrier can be moved, one station being a liquid loading station and another station being a liquid dispensing station, a dispenser assembly mounted on the carrier and including an injector needle arranged, when at the liquid dispensing station to pass through an aperture in a part of the luminometer aligned with a test sample container therein, when the sample container is in a test chamber with which a photo-multiplier device communicates, and sealing means for preventing light from passing through said aperture into the luminometer, both when the needle extends through said aperture and when the needle has been withdrawn from said aperture.

Preferably the movable carrier is mounted on the luminometer and is movable transversely between the loading station in which liquid can be picked up by the injector needle from at least one reservoir, and the liquid dispensing station in which the injector needle is aligned with the aperture in the luminometer, the injector needle being movable also in a direction or plane differing from said transverse direction or plane, to enter said aperture in order to allow liquid to be dispensed into a sample container.

Conveniently the transverse movement is in a generally horizontal plane and the said differing direction of movement is in a substantially vertical plane.

Conveniently the injector needle is a hollow tubular element having an internal dimension of a size enabling liquid to remain therein through surface tension, said element having at its lower end an injection outlet, and at the other end being connected to a tube whereby a column of liquid can be drawn into the injector needle and expelled therefrom, when required. This tube may be connected to a fluid source whereby positive or negative pressure can be built up in the injector needle to draw in or expel said liquid column.

Preferably the sealing means is arranged to exclude light from the vicinity of the said aperture in the luminometer when the injector needle is situated therein, as well as when the injector needle is away from the said aperture.

In one example the sealing means may comprise two sealing systems, one arranged to exclude light when the injector needle is in the aperture, and the other arranged to exclude light when the injector needle is away therefrom.

The said one sealing system may be arranged to take up a sealing position when the injector needle is brought to the liquid dispensing position. The said other sealing system may be arranged to actuate to close access to the said aperture in the luminometer through which the injector needle normally passes to the sample container position, when the injector needle is away therefrom.

In another example, the sealing means may include a diaphragm, through which the injector needle can pass to enter the said aperture in the luminometer and which seals around the needle, the diaphragm closing again when the injector needle is withdrawn therefrom, to provide a light tight seal in the vicinity of the said aperture.

Preferably the injection system also includes means for rinsing the injector needle, at a further station.

Controls are conveniently provided to move the carrier, and the injector needle on the carrier, as required. Such controls may be arranged to move the carrier and injector needle in a series of steps between liquid loading, dispensing stations and, where present, a rinsing station.

The apparatus may be controlled by a computer.

A further object of the invention is to provide a method of injecting liquid into a sample in a luminometer, the method being versatile, efficient, and in which the risk of extraneous light entry is minimised.

According to a further aspect, the invention provides a method of injecting liquids into a sample in a luminometer comprising the steps of bringing an injector needle, by means of a movable carrier, to a liquid loading station, causing a supply of liquid to be drawn into the injector needle, moving the carrier with the injector needle to a liquid dispensing station, passing the needle, in use, through an aperture in a luminometer, said aperture being aligned with a position of a test sample container in a test chamber in the luminometer with which a photo-multiplier device communicates, the movement of the injector needle at the liquid dispensing station being arranged to be accompanied by actuation of sealing means whereby light is excluded from entering the sample container when the needle is disposed therein, as well as when it is removed therefrom.

Conveniently the carrier and injector needle can occupy a rinsing station, at which a needle rinsing operation is carried out. Advantageously the rinsing operation includes drawing a rinsing liquid into the injector needle and discharging it to remove traces of other liquids, with which the needle may have been in contact.

The invention will now be described by way of example with reference to the accompanying drawings.

DESCRIPTION OF THE PREFERRED EMBODIMENTS

Figure 1:
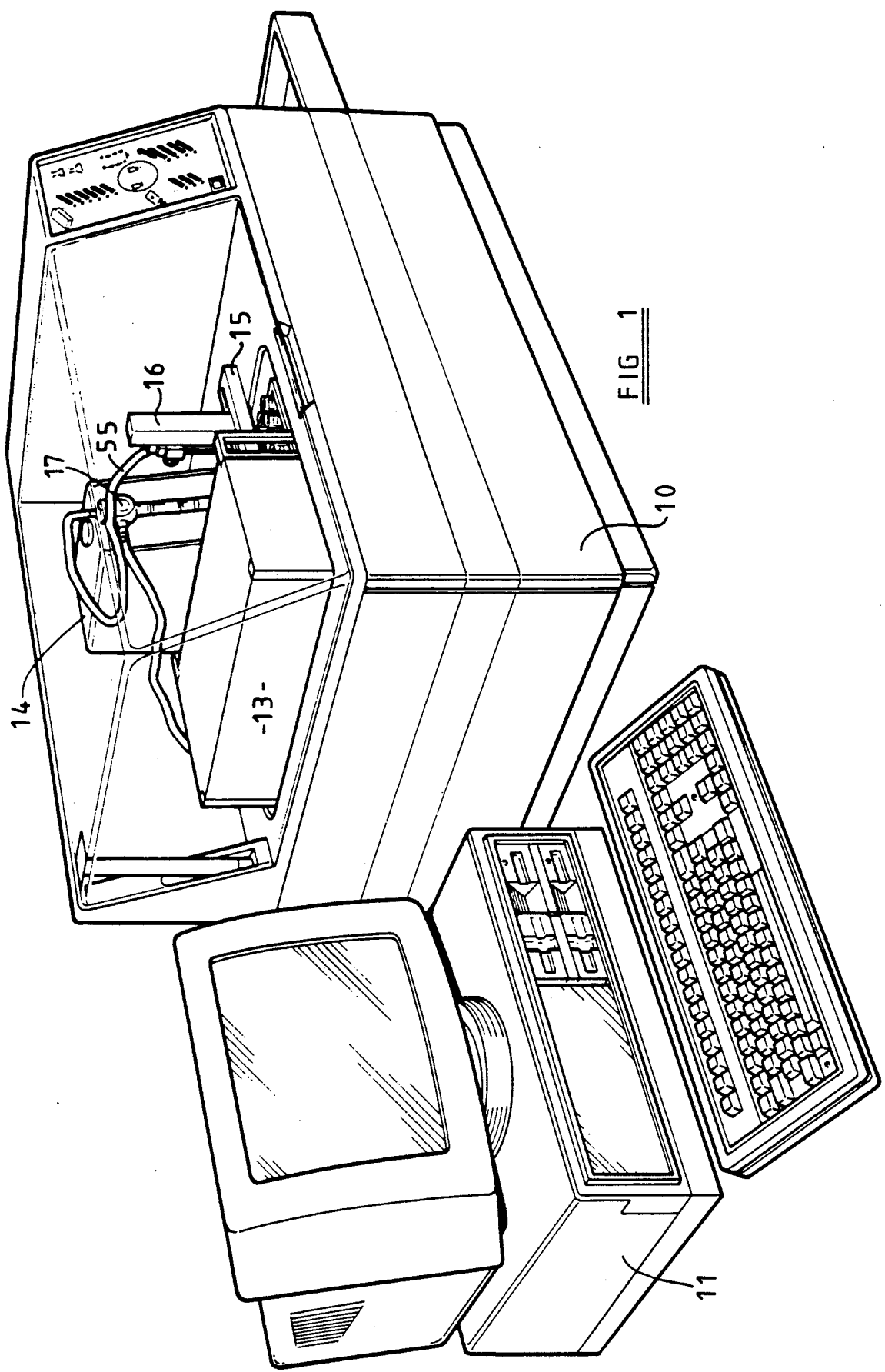
FIG. 1 is a perspective view of a luminometer and associated computer incorporating an injection system constructed in accordance with the invention.

The luminometer shown in FIG. 1 is of the kind described and claimed in published European Application No. 0226374. This is intended for the testing of liquids or liquid suspensions, these substances being contained within individual transparent cuvettes which are brought to the instrument in turn. A cuvette is typically of the kind shown in FIG. 2, at 9, and has a cylindrical form with one end open and the other end of convex, preferably hemispherical, configuration.

The substance to be tested may be subjected to processes which may be bio-luminescent or chemi-luminescent, creating emission of light photons which are detected by a photo-multiplier device in the instrument.

The drawing shows an external housing 10 within which the luminometer is contained. Within the luminometer casing is mounted (not shown) a rotatable bowl which can be rotated about a vertical axis within a fixed outer bowl. The outer surface of the inner rotatable bowl has a generally frusto-conical shape with the narrower end downwards whereby the outer sides of the bowl are inclined downwardly at an angle of inclination, for example of 35°, to the vertical axis of rotation. At one position in the outer surface of the bowl there is defined a concave examination chamber of generally semi-elliptical profile. The internal surface of this chamber is reflective to maximise light collection by a photo-multiplier device.

The arrangement is such that the cuvette can extend downwardly through an opening in the bowl and into the examination chamber so that the sample can be positioned to coincide with the cusp of the semi-ellipse formed by the examination chamber. Positioned adjacent the chamber, when the latter is in the test position, is the photo-multiplier tube device. This is of highly sensitive type and requires to be screened from extraneous light or other discharge sources. The optical axis of the photo-multipler tube is perpendicular to the plane of the outer edge of the examination chamber, and is therefore coincident with the central major axis of the semi-ellipse formed by the chamber.

An electric motor controls incremental rotational movement of the bowl from a loading position to a test position. Loading of cuvettes may be through a magazine system, and there is a cuvette handling mechanism whereby a series of cuvettes can be brought to the machine for testing and removed therefrom, in turn.

A computer, indicated generally at 11, controls the operating sequences of the luminometer machine.

At the top of the machine there is provided an injection system which is arranged to inject reagents or reactants into the sample-containing cuvettes when the latter are positioned in the test position of the luminometer. By this means it is possible to add to the sample one or more substances which can produce luminescence to be picked up immediately by the photo-multiplier tube, since the test sample will be in alignment with the photo-multiplier tube at the time of injection.

It is possible to inject more than one substance in a manner which will be described.

Figure 2:
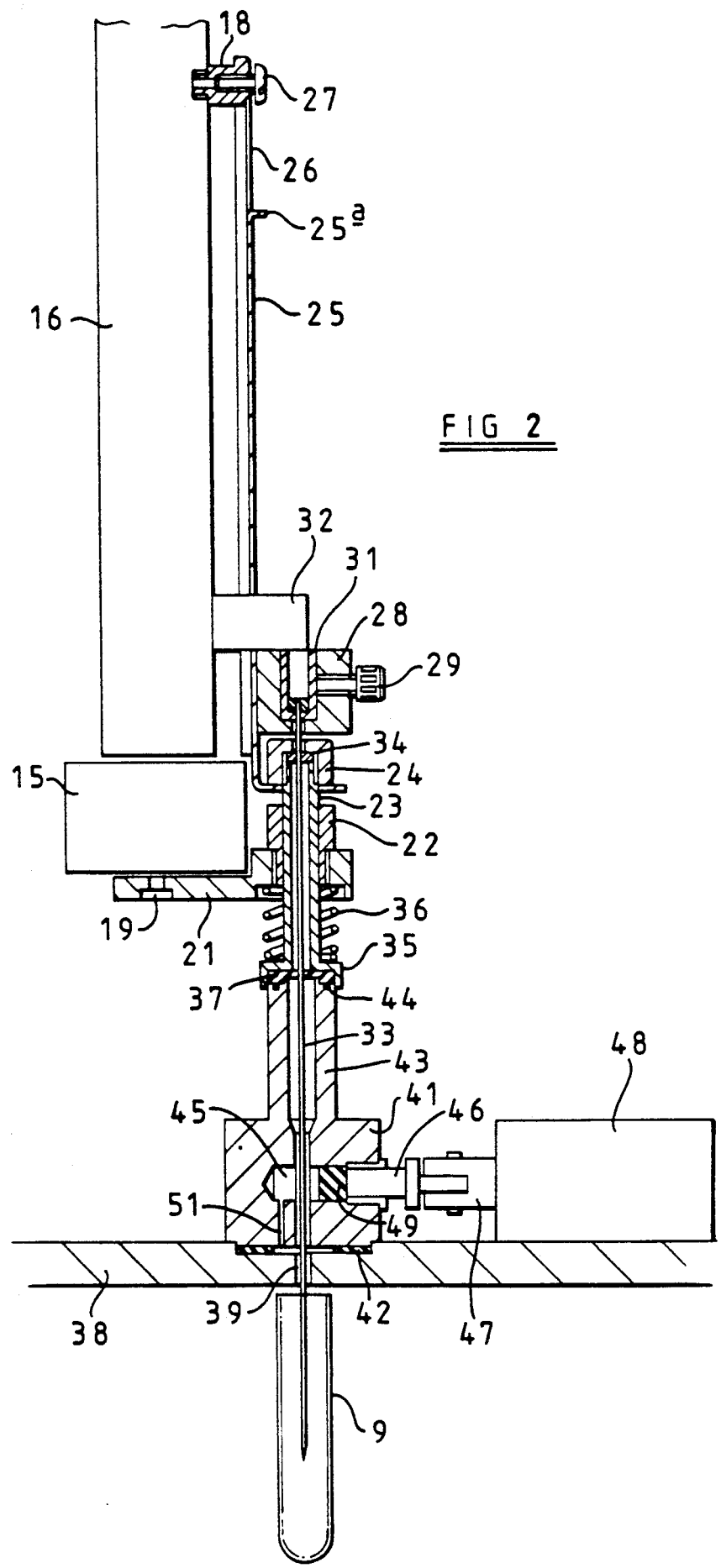
FIG. 2 is a cross-sectional view in a vertical plane of the injector system.

The injector system shown in FIG. 2 is mounted on a movable carrier including a horizontal arm 15 and a vertical column 16 which are movable under the control of a device contained within a housing 13 within the luminometer casing 10. The arm 15 can be moved lengthwise along the right-hand side of the housing 13, and therefore in the direction of the depth of the luminometer, and the column 16 can be moved lengthwise of the arm 15 and thus in the direction of the width of the luminometer. In this way it is possible for parts carried on the column 16 to be moved to any position within the area to which the limits of travel of the arm and of the column allow access.

A unit 14, also carried on the top of the luminometer, provides means whereby positive or negative fluid pressure, particularly air pressure, can be created, and on the front of the unit 14 is a rotary valve 17.

As seen in FIG. 2, the injector system is secured to the column 16 by a top fixture 18. The injector is also slidably connected, through a screw fitting 19, with the underside of the arm 15. The screw fitting 19 is carried in a bracket 21 in which is engaged a bush 22 supporting a vertical tube 23. Secured to the top of the tube 23 by a collar 24 is a slotted plate 25. The vertical slot 26 in the plate 25 is near its upper end, and the fixture 18 carries a screw 27 passing through the slot 26. A lug 25a is bent out of the plate 25 at the lower end of the slot 26.

A carrier 32 is mounted on the column 16 for sliding movement vertically along the column, under the control of the aforementioned control device within he housing 13. Mounted on the carrier 32 is a part 28 in which is secured, by means of a screw 29, a needle holder 31.

Carried by the needle holder 31 is a hollow needle 33. Its upper end is secured in the needle holder 31, which also serves as an adaptor to secure the end of a tube (not shown in FIG. 2), the interior of which is to communicate with the interior of the needle 33. The needle passes through a seal 34 which is trapped between the collar 24 and the end of the tube 23. The needle is a sliding fit in this seal.

The carrier 32 is shown in its lowermost position on the column 16 in FIG. 2. Its initial movement upwardly from this position, together with the part 28, needle carrier 31 and needle 33, takes place relatively to the slotted plate 25. However, when the carrier 32 engages the lug 25a on the plate 25, continued upward movement of the carrier also carries the plate 25 upwardly, together with the collar 24 and tube 23.

The lower end of the tube 23 is formed with a circular external flange 35 which is lipped to define a downwardly presented shallow recess. Located in the recess formed by the lipped flange 35 is a sealing ring 37 through which the needle 33 passes. Between the back of the flange 35 and the underneath surface of the bracket 21 is a helical compression spring 36 which tends to urge the tube 23 in a downward direction relatively to the bracket 21.

FIG. 2 also shows the upper wall 38 of the luminometer casing, and an aperture 39 formed therein. Engaged over the aperture 39 and secured to the upper wall 38 is a seal block 41. The lower end of the seal block is engaged in a recess in the wall 38 which also contains a sealing washer 42. Extending upwardly from the main portion of the seal block 41 is a tubular extension 43, in the upper circular end of which is located a sealing ring 44. The upper end of the tubular extension 43 is received in the aforementioned shallow recess provided by the lipped flange 35.

In a lateral bore 45 in the seal block 41 is located a piston 49 carried by a piston rod 46 connected to a plunger 47 of an electrical solenoid device 48 which is mounted on the upper surface of the wall 38 of the luminometer casing. Leading downwardly from the closed end of the bore 45 is a small communicating passage 51 which opens into the recess containing the sealing washer 42, but is in communication with the aperture 39 and thus with the interior of the luminometer casing.

In FIG. 2, the needle 33 is shown in its lower position in which its lower end is within a cuvette 9 which is illustrated in the position which it occupies when in the test position of the luminometer and opposite the photomultiplier tube.

The needle 33 can be withdrawn by appropriate actuation of the control device within the housing 13 to raise the carrier 32. It moves in two stages, the first bringing the needle upwardly out of the cuvette 9 through the aperture 39 in the wall 38 and to a position above the transverse bore 45 containing the solenoid piston 49. Although the needle 33, needle holder 31 and part 28 have been raised by the carrier, the slotted plate 25 and tube 23 remain stationery, and the compression spring 36 maintains a seal between the sealing ring 37 in the lower end of the tube 23 and the sealing ring 44 carried in the top of the tubular extension of the seal block 41. Travel of the needle is stopped at the end of its first stage of upward movement and the solenoid 48 is actuated to drive its piston 49 into the closed end of the bore 45. This has the effect of blocking the vertical passage through the seal block 41, through which the needle would travel in its downward movement. The second stage of upward movement is now carried out in which the carrier 32, as well as continuing to raise the needle 33, also raises the plate 25 (as a result of engaging the lug 25a) together with the collar 24 and the tube 23. The extent of this second stage of upward movement is determined by the length of the slot 26. This movement is sufficient not only to lift the end of the needle 33 out of the tubular upward extension 43 of the seal block 41, but also to separate the sealing ring 37 from the sealing ring 44. Such movement compresses the spring 36.

As the sealing ring 37 is separated from the upper end of the extension 43, the piston 49 effectively blocks any possible path for light entering the luminometer through the extension 43 and the opening 39 in the upper wall of the luminometer casing.

When the needle 33 is to be reinserted for injection into the cuvette 9, the first stage of downward travel is the reverse of that described, i.e. sufficient to introduce the needle into the tubular extension 43 of the seal block 41 and to bring the sealing ring 37 into contact with the sealing ring 44. These seals now block any possible access for light into the seal block 41, and thus it is possible to remove the piston 49 from its blocking position to the position shown in FIG. 2 without risk of entry of light into the luminometer. The second stage of downward movement then takes the needle into the position shown in FIG. 2 in which its end is protruding down into the cuvette 9.

Figure 3:
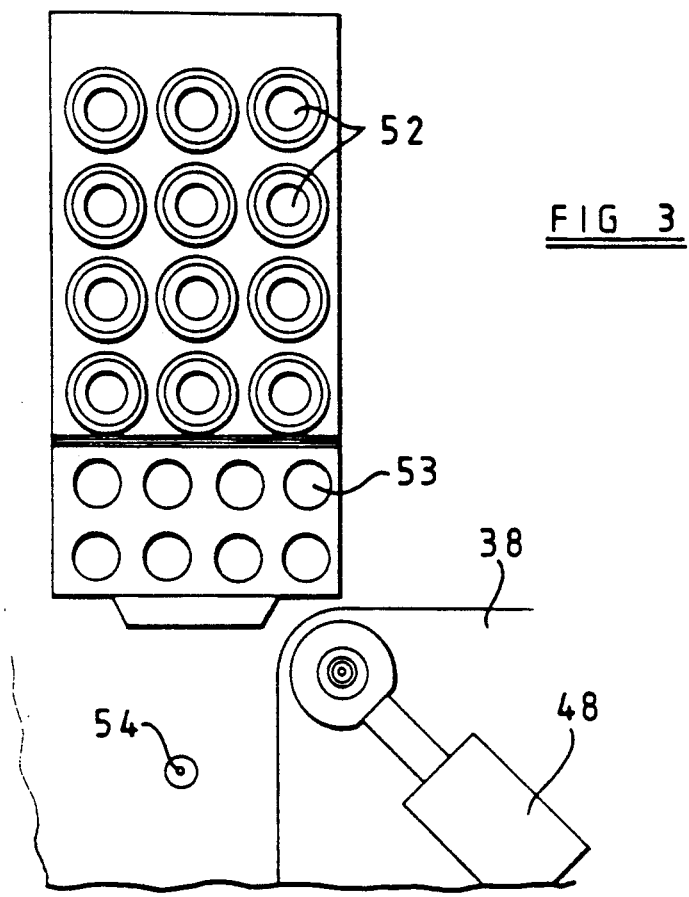
FIG. 3 is a plan view of part of the luminometer and injection system.

FIG. 3 shows the top wall 38 of the luminometer casing with the solenoid 48 mounted adjacent the position at which the needle passes through the aperture 39 in the wall 38. The movable mounting assembly for the injector system is not illustrated, but the travel of the arm 15 and of the column 16 are such that the needle can be positioned over any one of a series of stations, in some of which are reagent containers such as 52, or other liquid containers indicated at 53. Furthermore there is also a pre-treatment station at 54 at which the needle can be positioned.

The arrangement is such that the needle is positioned over one of the containers 52 or 53 and a procedure is followed to cause liquid to be taken up into the needle. This procedure comprises applying negative fluid pressure to the top of the needle holder 31, by means of a flexible tube 55 which leads from the needle holder 31 to the rotary valve 17 on the aforementioned unit 14.

The needle is now moved by appropriate movements of the arm 15 and column 16, to a position over the seal block 41, as seen in FIG. 2, and then, by means of the two stage lowering procedure already described, the needle is lowered into the cuvette. At this point, positive fluid pressure is applied through the tube 55 to discharge the liquid from the needle into the cuvette. The rotary valve 17 has positions enabling these positive and negative pressures to be applied. The rotary valve may be operated by a motor also connected to the aforementioned control device, and programmable by means of the computer 11 to provide the required movements in sequence.

When discharge of the liquid from the needle has taken place and the needle 33 has been lifted out of the cuvette, and after the light seal has been created by closing the piston 49 into the bore 45 of the seal block 41, the needle may be rinsed at a further station (not illustrated). Conveniently the rinse station is an elongate trough so that the needle can take up a position anywhere over the trough. Water or other cleansing fluid is drawn into the needle by application of negative pressure and is then discharged into the trough for drainage. Provision is made to ensure against contamination.

It is possible by means of this apparatus to provide several injections of differing substances into the same cuvette, the number of such substances being limited only by the space available for containers such as those shown at 52 and 53 in FIG. 3.

Figure 4:
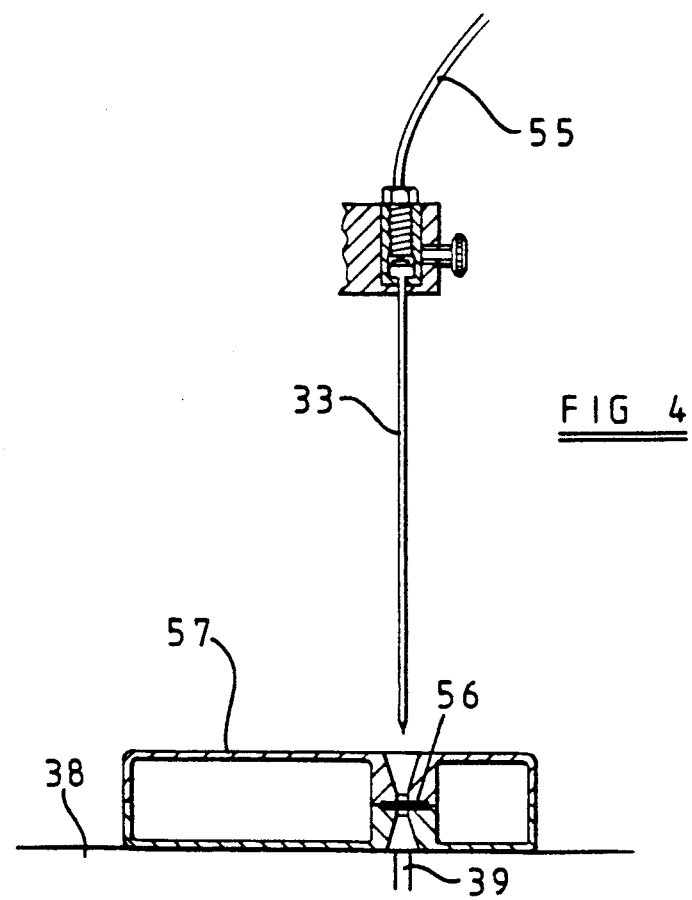
FIG. 4 is a fragmentary view of an alternative form of injector system constructed in accordance with the invention.

FIG. 4 illustrates an alternative device in which the needle 33, which is mounted in a manner similar to that shown in FIG. 2, communicates with the opening 39 in the wall 38 through a membrane 56 mounted in a support 57. The membrane 56 may be made of a resilient material which can be readily punctured by the sharpened end of the needle 33 during its downward travel. The material must re-close as soon as the needle is withdrawn to ensure a light tight seal. The membrane 56 may be part of a continuous strip which can be incrementally moved forward to provide a new unpunctured zone beneath the needle at each downward travel thereof.

The movement of the needle is simplified in such an arrangement, since it does not require the two stage movement necessary in the other construction already described. However, light tightness is entirely dependent upon the ability of the material of the membrane 56 to close immediately upon withdrawal of the needle.

What is claimed is:

1. An injection system in combination with a luminometer, comprising a movable carrier, there being at least two stations between which the carrier can be moved, one station being a liquid loading station and another station being a liquid dispensing station, a dispenser assembly mounted on the carrier and including an injector needle arranged, when at the liquid dispensing station, to pass through an aperture in a part of the luminometer aligned with a test sample container therein, when the container is in a test chamber with which a photo-multiplier device communicates, and sealing means for preventing the light from passing through said aperture into the luminometer, both when the needle extends through said aperture and when the needle has been withdrawn from said aperture, wherein the sealing means comprises first and second parts each having a through bore therein, the first part being in use fixed relative to the luminometer with its through bore aligned with said aperture in the luminometer and one end of the first part in light sealing relationship with said aperture, and the first part having a piston movable therein in a direction transverse to its through bore for selectively blocking the passage of light through its through bore, the second part being supported relative to the carrier and having one end in permanent light sealing relationship with the needle, the other end of the second part being movable into light sealing relationship with the other end of the first part as the needle approaches said aperture in the luminometer, said light sealing relationship occurring before the needle reaches the piston so that the piston can be moved to allow the needle access to said aperture after the first and second parts have been moved into light sealing relationship with one another.

2. An injection system as claimed in claim 1, further comprising spring means for urging the second part to a position in which it will in use maintain light sealing relationship with the first part until the needle has been withdrawn from said aperture in the luminometer and beyond the blocking means.

3. An injection system as claimed in claim 1, wherein the injector needle is a hollow tubular element having an internal dimension of a size enabling liquid to remain therein through surface tension, said element having at its lower end an injection outlet, and at the other end being connected to a tube whereby a column of liquid can be drawn into the injector needle and expelled therefrom, when required.

4. An injection system as claimed in claim 1 in combination with a luminometer, the movable carrier being mounted on the luminometer for movement transversely between said liquid loading station in which liquid can be picked up by the injector needle from at least one reservoir and said liquid dispensing station in which the injector needle is aligned with said aperture in the luminometer, the injector needle being movable also in a direction or plane differing from the transverse direction or plane, to enter said aperture in order to allow liquid to be dispensed into a sample container.

5. The combination as claimed in claim 4, wherein the transverse movement is in a generally horizontal plane and the said differing direction of movement is in a substantially vertical plane.

6. The combination as claimed in claim 4, wherein the injection system also includes means for rinsing the injector needle, at a further station.

* * * * *